US012281208B2

(12) United States Patent
Xu et al.

(10) Patent No.: US 12,281,208 B2
(45) Date of Patent: Apr. 22, 2025

(54) BIOACTIVE PLASTICS WITH PROGRAMMABLE DEGRADATION AND MICROPLASTIC ELIMINATION

(71) Applicant: The Regents of the University of California, Oakland, CA (US)

(72) Inventors: Ting Xu, Berkeley, CA (US); Christopher DelRe, Berkeley, CA (US); Junpyo Kwon, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 544 days.

(21) Appl. No.: 17/844,026

(22) Filed: Jun. 19, 2022

(65) Prior Publication Data

US 2022/0340731 A1 Oct. 27, 2022

Related U.S. Application Data

(63) Continuation of application No. PCT/US2021/012108, filed on Jan. 4, 2021.

(60) Provisional application No. 62/957,307, filed on Jan. 5, 2020.

(51) Int. Cl.

| | |
|---|---|
| ***C12P 17/08*** | (2006.01) |
| ***C08J 11/10*** | (2006.01) |
| ***C08L 67/04*** | (2006.01) |

(52) U.S. Cl.
CPC ............ *C08J 11/105* (2013.01); *C08L 67/04* (2013.01); *C12P 17/08* (2013.01); *C08J 2367/04* (2013.01)

(58) Field of Classification Search
CPC ............ C12N 9/20; C08J 11/10; A61K 47/34
See application file for complete search history.

(56) References Cited

U.S. PATENT DOCUMENTS

| | | | | |
|---|---|---|---|---|
| 2009/0162337 | A1 | 6/2009 | Gross | |
| 2024/0026114 | A1 * | 1/2024 | Xu | C12N 9/20 |

FOREIGN PATENT DOCUMENTS

| | | |
|---|---|---|
| EP | 1911472 | 4/2008 |
| WO | 2019143578 | 7/2019 |

OTHER PUBLICATIONS

Shohana Islam et al., Targeting microplastic particles in the void of diluted suspensions, Environment International, 123(2019) 428-435.
Written Opinion for priority PCT/US21/12108, filed Jan. 4, 2021) 9 pages (Apr. 16, 2021).
Extended European search report for related EP 21736205.2, 11 pages (May 31, 2023).

* cited by examiner

*Primary Examiner* — Tekchand Saidha
(74) *Attorney, Agent, or Firm* — Richard Aron Osman

(57) ABSTRACT

Nanoscopic dispersion of trace enzymes and random heteropolymers in plastics provides to fully functional plastics with eco-friendly microplastic elimination and programmable degradation.

19 Claims, 9 Drawing Sheets

50 μm 0.5 μm 2 hour
3 hour
6 hour
1 week
200 μm
200 μm
200 μm
200 μm 6 hour
100 μm
50 μm Fig. 9
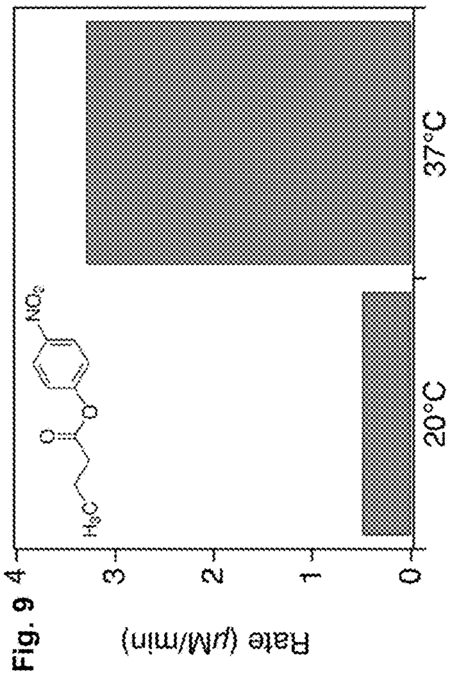
Fig. 10
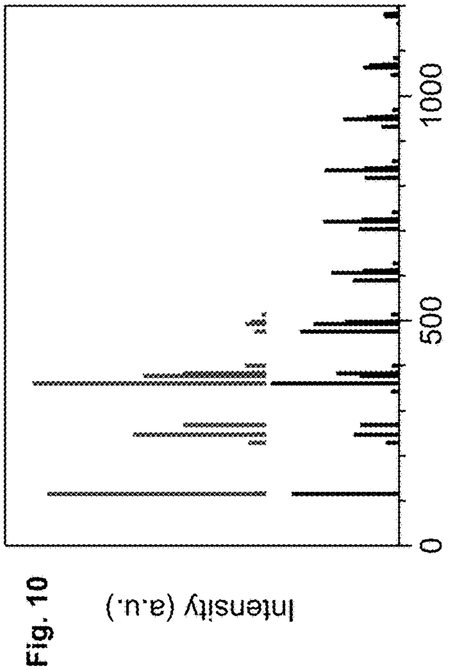
Fig. 11
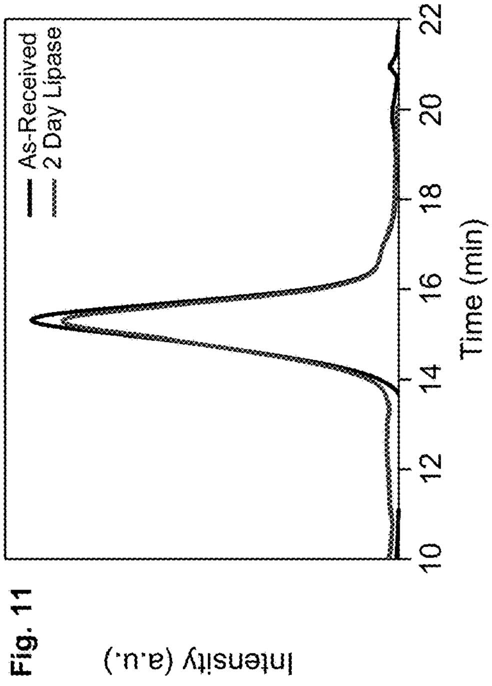
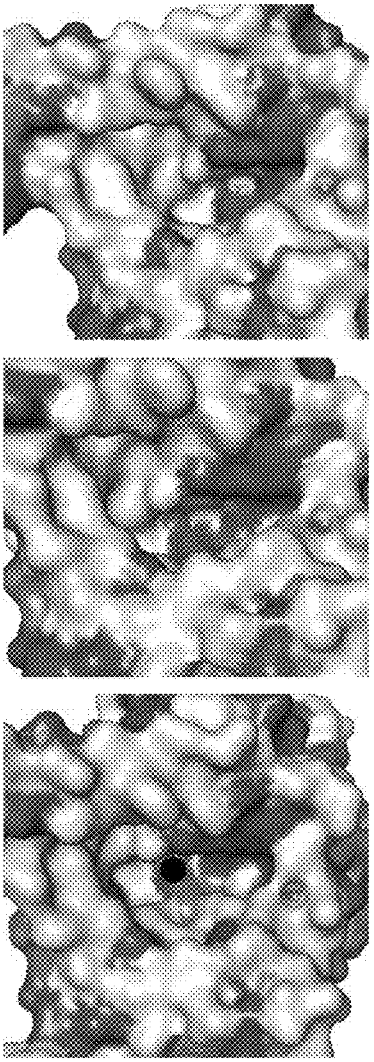
Fig. 12

Fig. 13
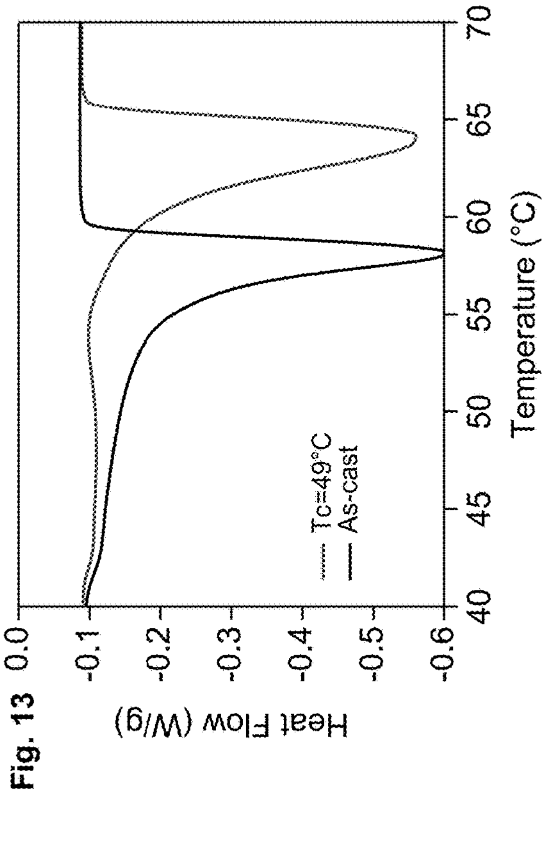
Fig. 14
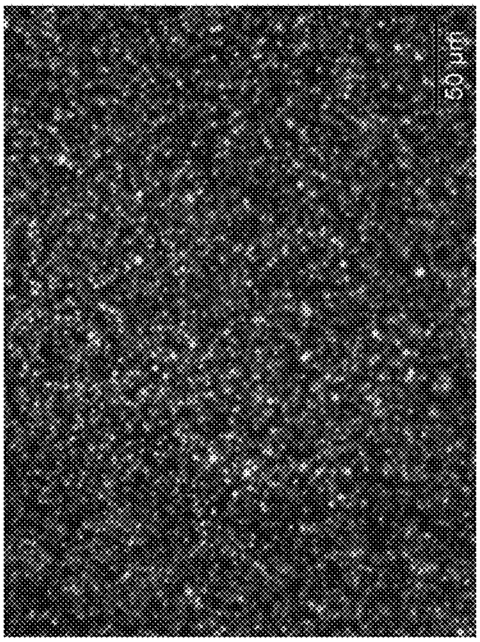
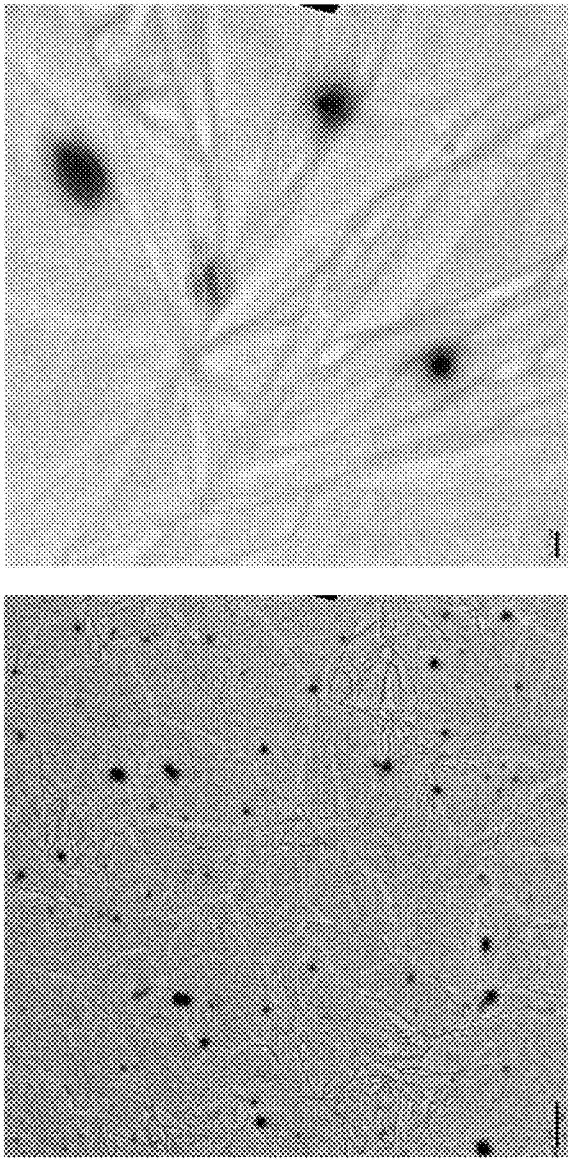
Fig. 15

Fig. 16
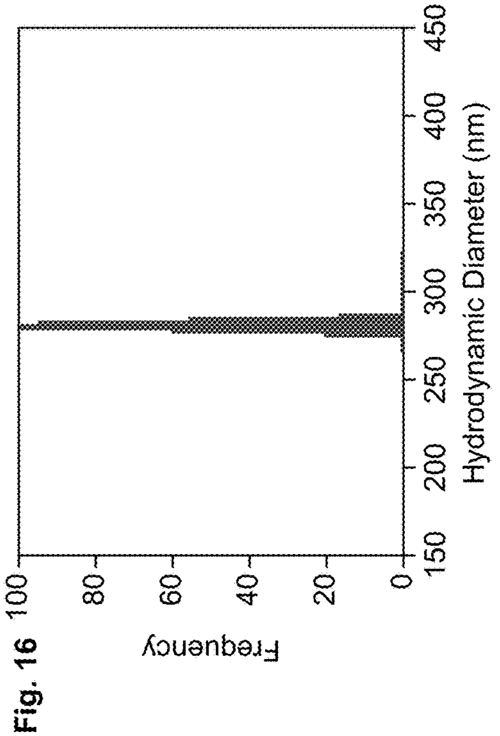
Fig. 17
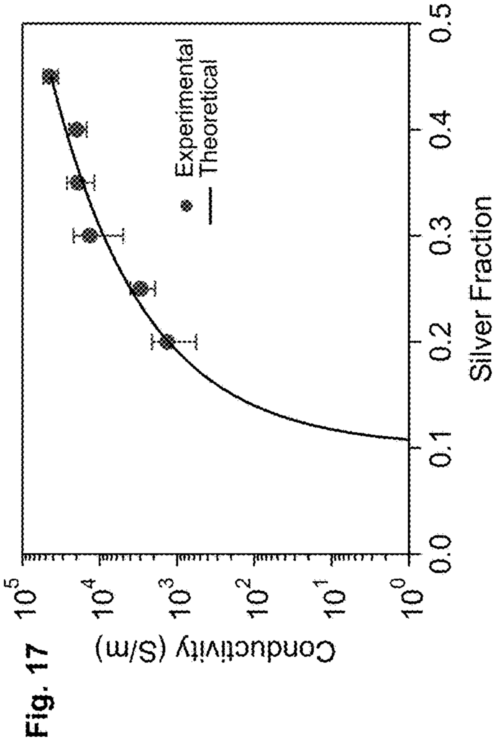
Fig. 18
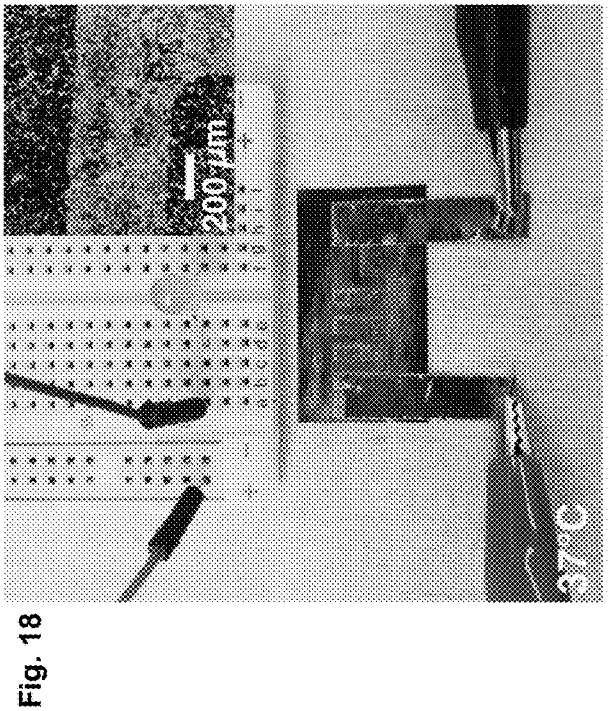
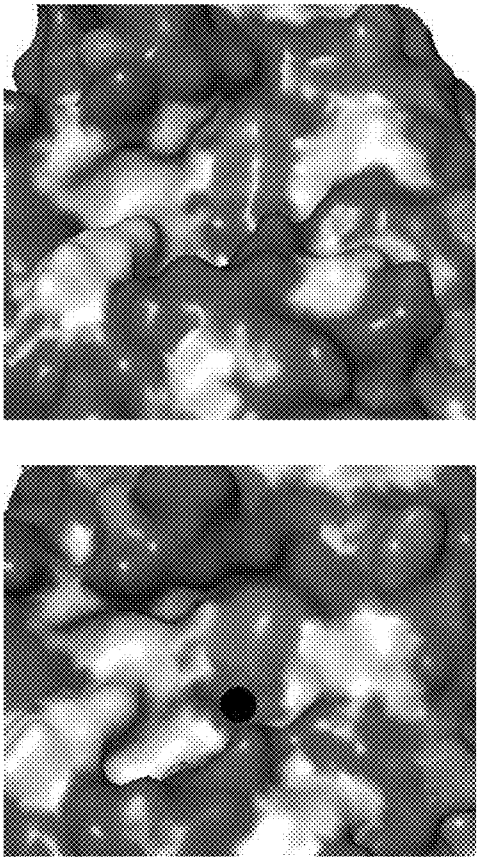
Fig. 19

BIOACTIVE PLASTICS WITH PROGRAMMABLE DEGRADATION AND MICROPLASTIC ELIMINATION

This invention was made with government support under: Grant Number W911NF-13-1-0232 by the Department of Defense, Army Research Office, and Grant Number DE-AC02-05CH11231 from the Department of Energy. The government has certain rights in the invention.

INTRODUCTION

As useful as polymers are, the burden of plastic waste has reached a breaking point, requiring immediate collaboration from all communities. Effective microplastic elimination is a newly-recognized challenge with no immediate solution despite years of efforts in plastic recycling.[1] Plastic waste that has accumulated in landfills[2] and oceans[3] breaks down into microplastics that are then ingested by various species and transferred up the food chain,[4,5] posing serious health concerns for humans and wildlife. New plastic materials with controllable degradation and rapid microplastic elimination must be created within the existing manufacturing framework to improve chemical recycling efficiency and remain economically feasible.

Enzymes catalyze recycling processes of materials in landfills and aquatic systems;[6] however, this external degradation process takes years due to low concentration of available enzyme and diffusion-limited surface erosion via random chain scission.[7,8] Embedding catalysts capable of cleaving polymer chains can accelerate plastic degradation.[9,10] Physical enzyme encapsulation has resulted in limited success in programmable plastic degradation but no effect in microplastic elimination. Enzymes aggregate and lose significant activity during either solution- or melt-based polymer processing[11] and leach out when the host disintegrates.[12] Nanoscopic enzyme dispersion increases enzyme availability and degradation efficiency, reduces leaching and ensures continuous degradation upon microplastics formation. Although little is known in solid-phase enzymology once encapsulated in the dimension comparable to that of a single polymer chain, it may be feasible to modulate enzyme-host interaction and polymer degradation to achieve molecular control over by-products toward a closed-loop lifecycle.

Our prior WO2019143578 discloses that random heteropolymers can preserve protein function in foreign environments. US20180142097 relates to biodegradable polyester that uses random scission. Our programmable degradation process relies on exploiting the enzymes' active site geometry and surface chemistry to manipulate the enzyme-polyester interactions to make the degradation processive/single chain.

SUMMARY OF THE INVENTION

We disclose that nanoscopic dispersion of trace enzyme (e.g. lipase) in plastics (e.g. polycaprolactone) (PCL) leads to fully functional plastics with eco-friendly microplastic elimination and programmable degradation. Nanoscopic enzyme encapsulation leads to (1) continuous degradation to achieve 95% microplastic elimination; (2) polymer degradation mechanism with repolymerizable small molecule by-products via selective chain end scission rather than random chain scission; (3) spatially- and temporally-programmable degradation of melt-processed host matrix due to the dependence of polymer degradation on local lamellae thickness regardless of bulk percent crystallinity; (4) formulation of conductive ink for 95 The invention provides an environmentally friendly and technologically viable solution toward microplastic elimination and material recycling.

In an aspect the invention provides bioactive plastic composition comprising an organic polymer and a nanoscopic dispersion of complexes of random heteropolymers (RHPs) and an enzyme that hydrolyzes the polymer, such that hydrolysis of the polymer by the enzyme imparts programmable processive depolymerization and microplastic elimination.

In embodiments:

the complexes are uniformly distributed within the composition, the complexes range in size from 10, 20 or 40 nm to 100, 200 or 500 nm or ranging from 10, 20 or 40 nm to 100, 200 or 500 nm between the crystalline polymer lamellae, and/or the composition comprises 0.001, 0.01 or 0.1 to 0.1 or 1 or 5% enzyme content;

the RHPs comprising varying ratios a plurality of monomers selected from methyl methacrylate (MMA), oligo (ethylene glycol) methacrylate (OEGMA), 3-sulfopropyl methacrylate potassium salt (3-SPMA) and 2-ethylhexyl methacrylate (2-EHMA);

polymer/enzyme combinations are selected from selected from polycaprolactone (PCL)/lipase, polylactic acid (PLA) proteinase K, and polyethylene terephthalate (PET)/PETase.

the composition is formulated in a conductive ink for 3-D printing with substantial (50, 60, 70, 80 or 90% to 90, 95 or 99%) recovery of the precious metal filler;

the composition is configured to provide continuous degradation to achieve 65, 90, 95 or 99% microplastic elimination;

the composition is configured to provide a polymer-based degradation mechanism with repolymerizable small molecule by-products via selective chain end scission rather than random chain scission; and/or the composition is configured to provide spatially- and temporally-programmable degradation of processed (melt-processed or solution-processed) host matrix due to the dependence of single chain degradation on local lamellae thickness regardless of bulk percent crystallinity.

In an aspect the invention provides a method of programmable degradation comprising providing a disclosed composition, under conditions wherein the enzyme cleaves the polymer backbones (hydrolyzes the polymer), imparting programmable degradation and microplastic elimination.

The invention encompasses all combination of the particular aspects and embodiments recited herein, as if each combination had been laboriously recited.

BRIEF DESCRIPTION OF THE DRAWINGS

FIG. 9: Hydrolysis rate of 4-nitrophenyl butyrate by PCL-RHP-lipase at 20° C. and 37° C.

FIG. 10: Mass spectra of PCL-RHP-lipase (blue) and pure PCL in concentrated lipase blend solution (black).

FIG. 11: GPC of PS-PCL-PS after lipase treatment; additionally, no mass change of film after lipase treatment was detected using a balance, further supporting lack of degradation.

FIG. 12: Different angles of lipase active site in PyMOL (white represents hydrophobic amino acids, purple represents polar noncharged amino acids, blue represents positively charged amino acids, and red represents negatively charged amino acids); the catalytic serine residue is marked with a black dot in the image on the left for reference.

FIG. 13: DSC curves of PCL-RHP-lipase with different recrystallization conditions.

FIG. 14: Fluorescence microscopy image of PCL-RHP-lipasecb.

FIG. 15: TEM images of PCL-RHP-lipasecb in a PCL matrix.

FIG. 16: DLS of RHP-lipasecb in toluene.

FIG. 17: Conductivity measurements of 3-D printed PCL-RHP-lipase-silver circuits as a function of silver content.

FIG. 18: PCL-RHP-lipase-silver circuits after 4-hour incubation in a 37° C. buffer demonstrating minimal electrical conductivity due to degradation; (inset) SEM image showing disruption of silver flake network due to PCL matrix degradation.

FIG. 19: Different angles of proteinase K active site in PyMOL; white represents hydrophobic amino acids, purple represents polar noncharged amino acids, blue represents positively charged amino acids, and red represents negatively charged amino acids); the catalytic serine residue is marked with a black dot in the image on the left for reference

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or. The examples and embodiments described herein are for illustrative purposes only and various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Here we show that nanoscopic enzyme dispersion in plastics can effectively eliminate microplastics without compromising polymer processing and macroscopic properties, using a random heteropolymer (RHP) approach.[13,14] With enhanced enzyme availability and stabilization, the addition of a trace amount of enzyme (e.g. 0.02 wt % lipase in poly(caprolactone) (PCL)) eliminates ~95% of microplastics within 24 hours in water. Once encapsulated, lipase hydrolyzes PCL preferentially via chain-end scission (FIG. 1A) and generates non-toxic, repolymerizable small molecules. With nanoscopic dispersion, RHP-lipase demonstrates excellent thermostability required for melt processing. Controlled recrystallization from the melt, in turn, leads to temporally- and spatially-programmable degradation. In addition, these bioactive plastics can be used to formulate conductive inks to 3-D print fully functional electronics for recovery of precious metal fillers after continuous operation. Controlled plastic degradation via RHP/enzyme dispersion is applicable to other plastic/enzyme systems. Our disclosure validates bioactive plastics as a viable approach for effective plastic recycling and elimination of microplastics.

Figures 1A, 1B, 1C, 1D, 1E:
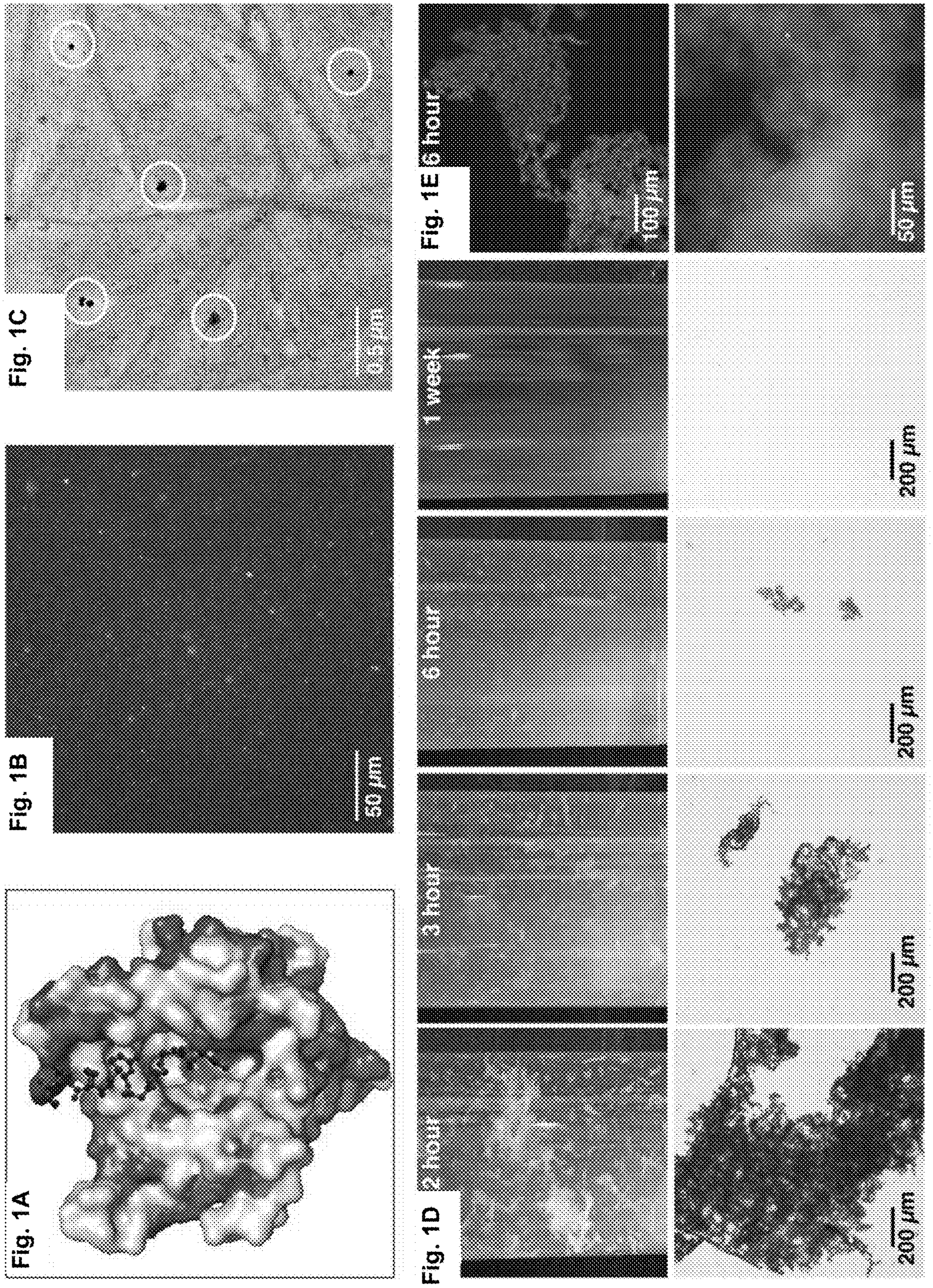
FIGS. 1A-1E. Characterization of PCL-RHP-lipase and microplastic elimination. A) Lipase crystal structure showing proposed preferential binding of PCL chain ends at the active site (hydrophobic amino acids in white, polar non-charged in purple, positively charged in blue, and negatively charged in red; for PCL, carbon atoms in dark gray, oxygen atoms in red, hydrogen atoms not shown); B) fluorescence microscopy image of a PCL-RHP-lipase film; C) TEM image showing RHP-lipase complexes dispersed in PCL semicrystalline matrix; D) photographs and optical images of PCL-RHP-lipase degradation over time in a 40° C. buffer; the film was briefly vortexed after 2 hours to facilitate physical disintegration into microplastics E) fluorescence microscopy image of PCL-RHP-lipase microplastic formed during degradation where green fluorescently labeled lipase is retained.
Figure 5:
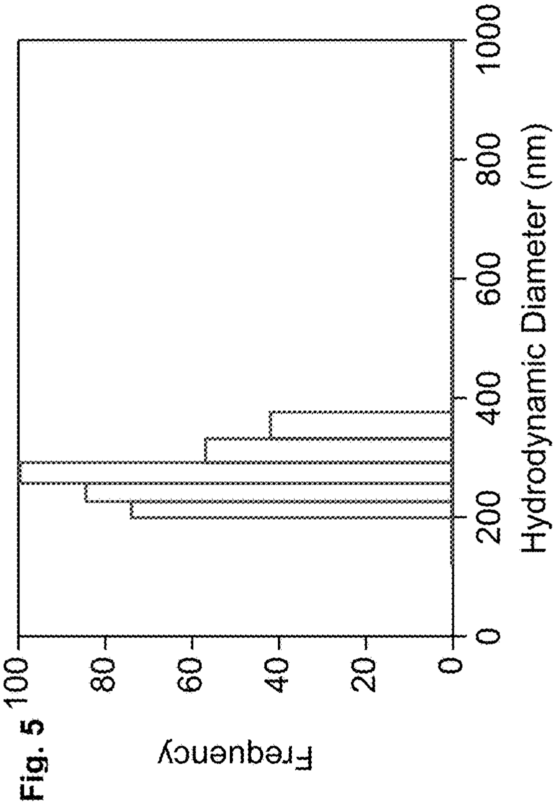
FIG. 5: DLS of RHP-lipase in toluene with an average hydrodynamic diameter of 285 nm±35 nm.
Figure 6:
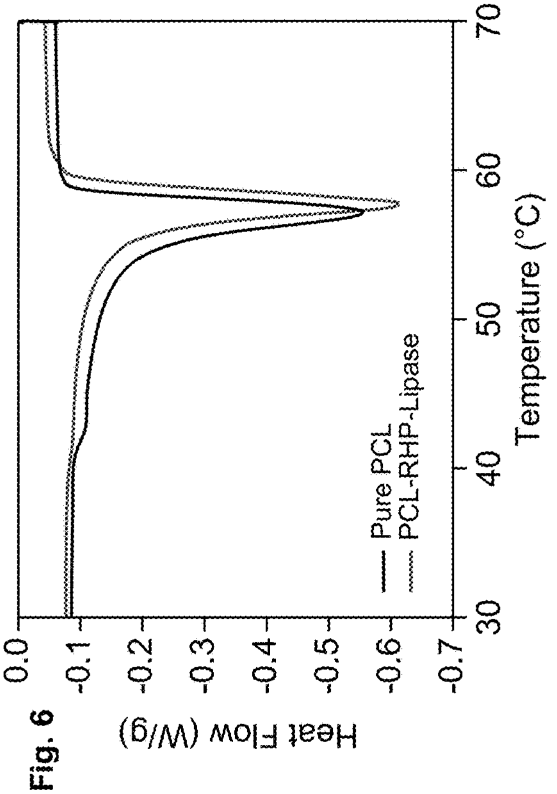
FIG. 6: DSC curves of pure PCL and PCL-RHP-lipase as-cast films.
Figure 7:
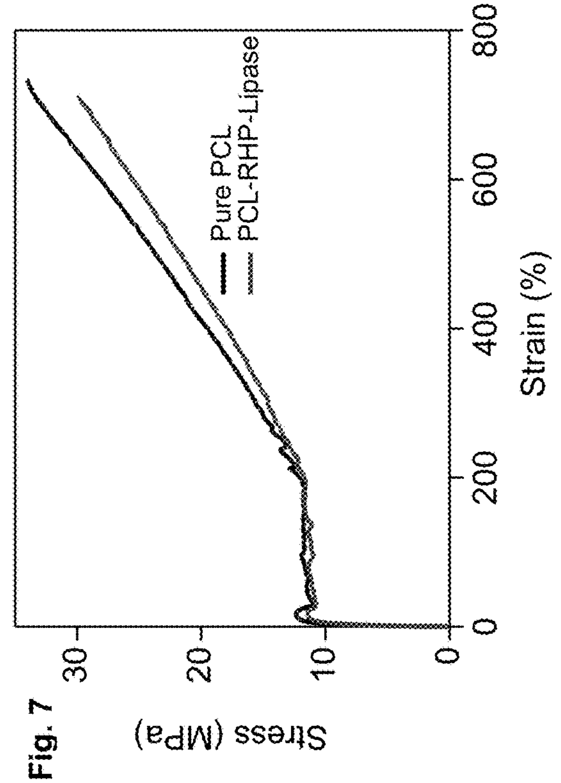
FIG. 7: Engineering stress-strain curves from uniaxial tensile tests of pure PCL and PCL-RHP-lipase.
Figure 8:
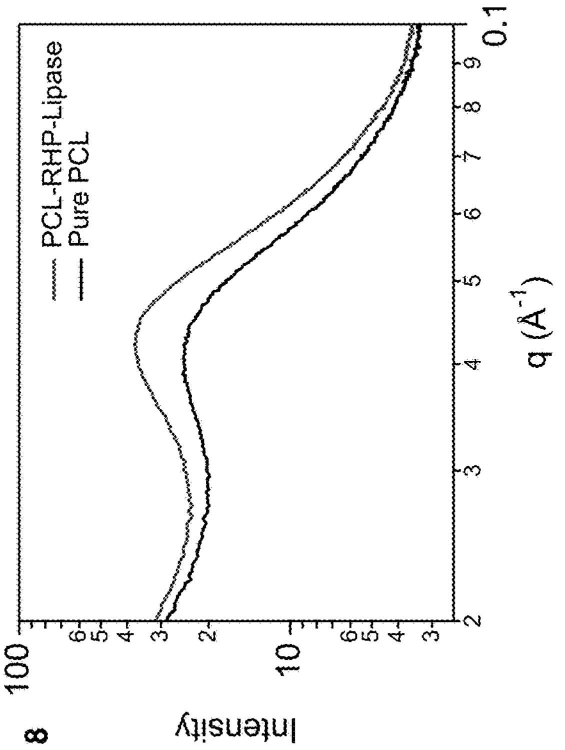
FIG. 8: SAXS profiles of pure PCL and PCL-RHP-lipase solution cast films.

Nanoscopic enzyme dispersion in plastics is essential to formulate functional bioactive plastics. However, enzymes form aggregates when mixing with host polymer and effective degradation requires enzyme concentrations as high as 10 wt %.[9] As the degradation proceeds, these enzyme aggregates leach out[15] and leave microplastics behind. RHP-lipase is well-dispersed in a range of solvents, forming ~285 nm complexes in toluene (FIG. 5) while pure lipase precipitates out. RHP-lipase is uniformly distributed in solution-cast PCL films as confirmed by fluorescence microscopy images (FIG. 1B). Transmission electron microscopy (TEM) images show nanoscopic dispersion of RHP-lipase complexes ranging from ~50 nm to ~500 nm between the crystalline PCL lamellae (FIG. 1*c*). With up to 2 wt % enzyme content, there are only minimal changes in PCL bulk percent crystallinity and mechanical properties (FIG. 6 and FIG. 7). Small angle x-ray scattering (SAXS) profiles show similar PCL crystallization with and without lipase incorporation (FIG. 8).

Semicrystalline PCL containing RHP-lipase (called "PCL-RHP-lipase") rapidly degrades once immersed in water. FIG. 1D shows a series of pictures of PCL-RHP-lipase film (0.02 wt % lipase) in a 40° C. buffer as a function of immersion time. As degradation proceeds, the PCL-RHP-lipase film disintegrates into microplastic particles. However, using fluorescently-labeled lipase, it is evident that the lipase remains embedded and well dispersed within PCL microplastic particles (FIG. 1E). Control experiments further confirm the lipase activity within microplastic and continuous PCL degradation. Approximately 95% of the microplastics are degraded to small molecule by-products after 24 hours, as estimated by gel permeation chromatography (GPC). We titrated down the enzyme concentration and obtain 95% degradation at 0.01 and 0.001 wt % lipase.

Figures 2A, 2B, 2C, 2D:
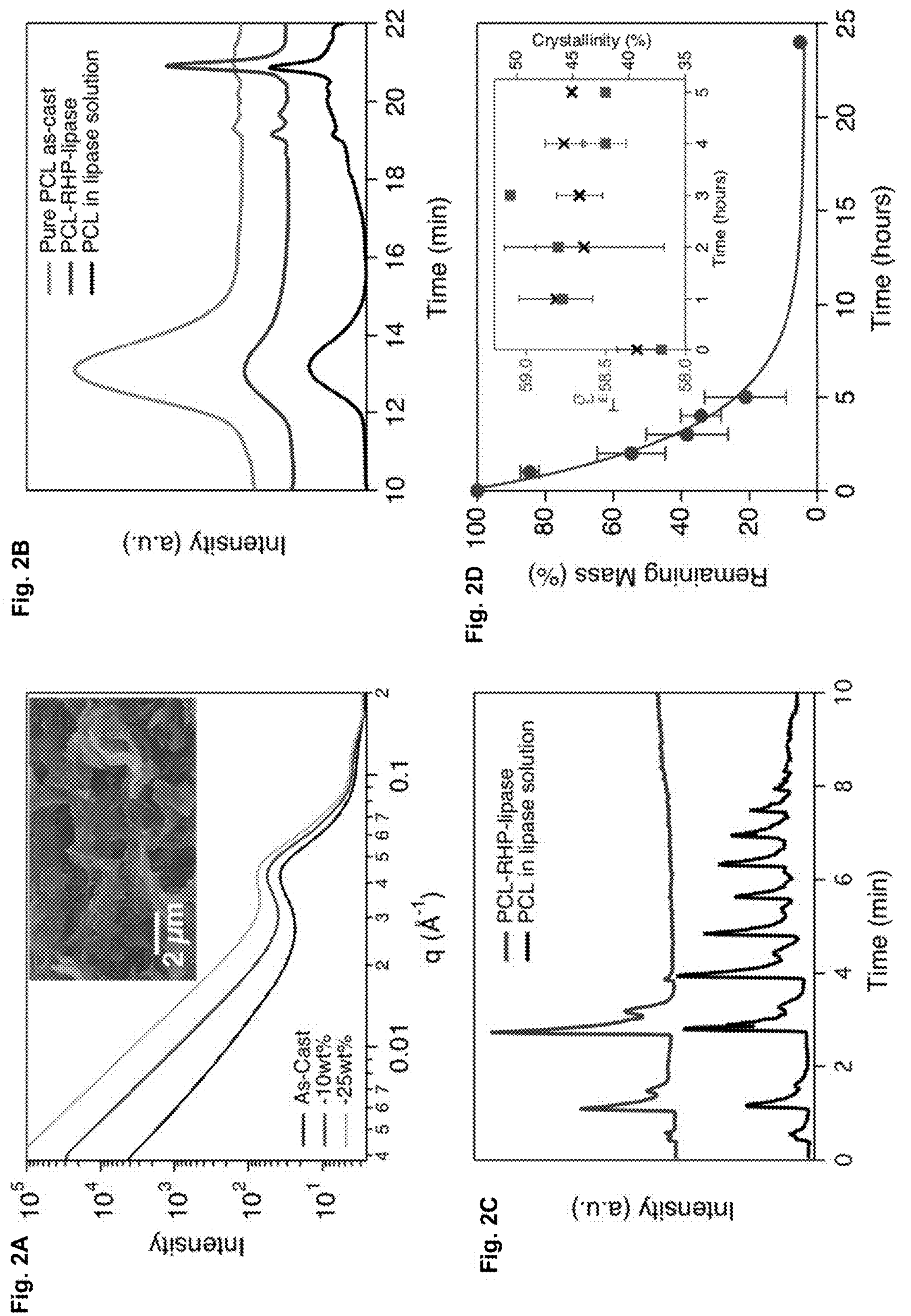
FIGS. 2A-2D. PCL-RHP-lipase degradation mechanism and well-defined by-products. A) SAXS profiles of PCL-RHP-lipase; (inset) cross-sectional SEM image of PCL-RHP-lipase after ~50% mass loss; B) GPC curves of pure PCL, degraded PCL-RHP-lipase in pure buffer, and degraded pure PCL in concentrated lipase solution; the degraded samples both have approximately 50% mass loss C) chromatogram of PCL-RHP-lipase and pure PCL in concentrated lipase solution; D) remaining mass as a function of time for PCL-RHP-lipase (inset) melting temperature (blue ■□) and percent crystallinity (black ✖) during first 5 hours of degradation (error bars represent standard deviation at each timepoint; n≥3 for degradation, n≥2 for DSC analysis in the inset); the 24 hour timepoint was estimated by integrating GPC peaks, while all prior timepoints were determined by drying and weighing the remaining films.

Understanding mechanistic details of PCL-RHP-lipase internal degradation from bulk down to the nanoscale can allow for better control over degradation and assist with future designs for other enzyme-embedded bioactive plastic. PCL-RHP-lipase degrades internally rather than via surface erosion. The films degrade at a similar rate regardless of buffer volume (1 mL to 1 L), which agrees with the design that degradation is catalyzed by embedded enzyme rather than enzyme leaching out and degrading from the surface. FIG. 2A shows SAXS profiles of PCL-RHP-lipase as-cast and up to ~25% mass loss. Intensity increased in the low q range as degradation proceeded due to the nanoporous structure formation as internal degradation proceeds. This agrees with the cross-sectional scanning electron microscopy (SEM) image (FIG. 2A inset).

PCL-RHP-lipase degradation displays a temperature dependence very much different from that of surface erosion process. Despite rapid internal degradation at 37° C., the degradation is negligible at 20° C. up to three months. However, lipase dissolved in solution is capable of degrading ~50% of PCL via surface erosion at 20° C. in a few days. Additionally, PCL-RHP-lipase is capable of hydrolyzing a small molecule ester in solution at 20° C. (FIG. 9), assuring lipase's activity and water accessibility. Limited degradation of PCL-RHP-lipase at 20° C. may be attributed to the interplay among substrate binding in the lipase active site, enzyme mobility/conformational flexibility within solid matrix and local PCL chains packing.

PCL-RHP-lipase degradation proceeds via preferential chain-end scission rather than random chain scission. GPC analysis shows that as degradation proceeds, the main PCL peak reduces in intensity but no notable formation occurs of polymer or oligomer with intermediate molecular weight (FIG. 2B), which is consistent with chain-end scission.[16] The primary by-products during PCL-RHP-lipase degradation are confirmed to be monomer and small oligomers (primarily <5 repeat caprolactone units) using liquid-chromatograph-mass spectrometry (LCMS) (FIG. 2C and FIG. 10). Shown for contrast in the GPC and LCMS chromatograms are by-products from external PCL degradation in concentrated lipase solution (0.1 mg/mL), where intermediate molecular weight by-products of at least 12 repeat units are seen (FIG. 10). The degradation mechanism was further probed by testing degradability of a PCL-based triblock capped on both ends with a small polystyrene (PS) block (PS-PCL-PS, 1,500-8,000-1,500 g mole-1). With similar treatment, PS-PCL-PS degradation was negligible after 2 days in a 37° C. buffer (FIG. 11). Lack of PS-PCL-PS degradability suggests that lipase binds to PCL chain ends in the solid state. The production of small, water-soluble degradation by-products is greatly beneficial. Monomers and small oligomers have better chemical recyclability compared to that of higher molecular weight by-products. As a proof of concept, by-products from PCL-RHP-lipase degradation were repolymerized into PCL.

Lipase's active site is analyzed to understand the experimentally-observed selective chain end scission. Analysis of the surface chemistry in the lipase active site shows that PCL can be selectively bound mainly via hydrophobic interactions, which are prevalent in lipase's binding pocket (FIG. 1A and FIG. 12). The lipase catalytic triad resides 1.7 nm from the surface, and the base narrows to 4.5 Å near the catalytic residue.[17] This deep and narrow active site might exclude bulky substrates and allow only the most mobile portions of PCL, the chain ends, to access the catalytic serine residue at the funnel base. Based on the dimensions of lipase and PCL chain conformation in the solid state, selective lipase binding to the PCL chain end should be preferred.

Changes in PCL crystalline properties during degradation provide further insight into the degradation mechanism on the nanoscale and suggest that local lamellae thickness affects degradation. From 0 to 1 hour, the bulk percent crystallinity increases from 39±1.8% to 47±2.0% (FIG. 2D inset, black x's) due to preferential amorphous degradation. However, between 1 and 5 hours the percent crystallinity does not change within experimental error despite the film mass being reduced from ~80% to just ~20% of its initial value, proving that lipase degrades crystalline domains. Additionally, the degradation curve is roughly linear between 0 and 3 hours, but the rate slows down near 3 hours. The melting temperature, which is directly proportional to average lamellae thickness for semicrystalline polymers, increases from 0 to 3 hours due to thermal annealing (FIG. 2D inset, blue squares). The degradation rate slows down near 3 hours—the peak observed melting temperature—apparently due to higher local enthalpic stability of the thermally-annealed thicker lamellae, which undergo enzymatic degradation. Furthermore, previous reports show that certain enzymes can assist with lowering the activation barrier for de-crystallizing single polymer chains and degrade them processively (i.e. consecutive hydrolysis reactions without releasing the polymer chain).[18,19] Lipase fits the common traits of processive enzymes, which are characterized by hydrophobic binding interactions and tunnel-like active sites that facilitate single-chain sliding while hindering dissociation.[18] The chain-end degradation mechanism combined with the dependence on lamellae thickness for PCL-RHP-lipase degradation can be explained by single-chain processivity given that single chains traverse both crystalline and amorphous domains in semicrystalline polymers.

Figures 3A, 3B, 3C, 3D:
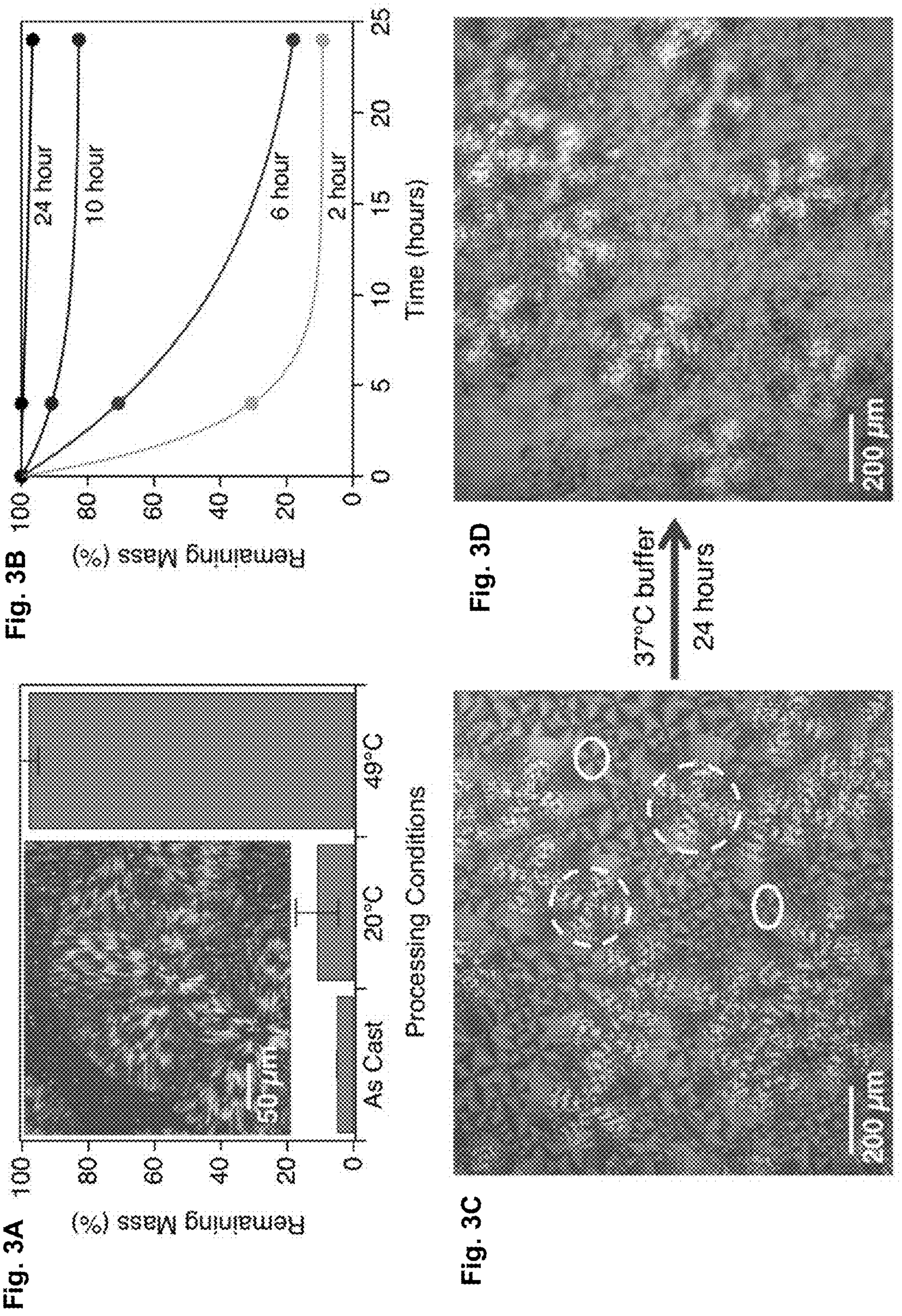
FIGS. 3A-3F. Temporal and spatial control of PCL-RHP-lipase degradation. A) Remaining mass after 24 hour degradation in a 37° C. buffer for PCL-RHP-lipase films cast from solution or melted for 5 minutes and recrystallized at given temperature (note that Tc=49° C. films exhibit negligible degradation up to 8 weeks); (inset) overlaid polarized and fluorescence images of PCL-RHP-lipase crystallized at 49° C.; B) degradation curves for PCL-RHP-lipase recrystallized at 49° C. for the stated time and then degraded in a 37° C. buffer; C) mixed-morphology PCL-RHP-lipase film recrystallized at 49° C. for 12 hours and then quenched at 20° C. (dashed circles represent spherulites grown at 49° C., solid circles represent spherulites grown at 20° C.); D) mixed-morphology film after undergoing degradation in a 37° C. buffer for 24 hours showing degradation of only the spherulites grown at 20° C.; e) degradation curves for different lipase blend concentrations; f) degradation curves for different PCL-RHP-lipase film thicknesses (error bars represent standard deviation at each timepoint, n for all).

The embedded lipase has enhanced thermostability—retaining 40% of its initial biological activity after 5 hours at 80° C. in the melt—and is compatible with melt processing. Overlaid polarized optical microscope and fluorescence microscope images (FIG. 3A inset) show that lipase is incorporated within crystalline spherulites rather than segregated interspherulitically, owing to the orders-of-magnitude slower enzyme diffusivity in the PCL melt compared to the crystal front growth rate. Despite similar enzyme distributions for all recrystallization temperatures, the different processing conditions significantly affect degradation. Films melted for 5 minutes (resulting in minimal enzyme activity loss) and recrystallized at 20° C. degrade similarly to solution-cast films, but films recrystallized at 49° C. exhibit minimal degradation after weeks in a 37° C. buffer (FIG. 3A). This difference in degradability might be attributable to differences in local thermodynamic stability of crystalline domains. The slow crystal growth rate at Tc=49° C. results in thicker lamellae and amorphous domains, as indicated by a ~6° C. increase in melting temperature despite a comparable bulk percent crystallinity to that of the as-cast film (FIG. 13). This large increase in local enthalpic stabilization due to thicker lamellae for Tc=49° C. films can make enzymatic degradation energetically unfavorable if degradation proceeds processively via single PCL chains. Contrarily, the Tc=20° C. films have similar lamellae thicknesses and similar degradation rates to the as-cast samples. The difference in degradation behavior for films recrystallized at 20° C. and 49° C. confirms that lamellae thickness is strongly correlated with degradability and is consistent with single-chain processive degradation mechanism for PCL-RHP-lipase.

Melt processing allows for both temporal and spatial control of PCL-RHP-lipase degradation. The degradation rate in a 37° C. buffer can be tuned by controlling PCL-RHP-lipase crystallization time at 49° C. (FIG. 3B). A film crystallized at 49° C. for 12 hours and then quenched at 20° C. exhibits two distinct crystalline morphologies (FIG. 3C). After placing the mixed-morphology film in a 37° C. buffer for 24 hours, only those regions crystallized at 20° C. exhibited degradation; the large spherulites that were grown at 49° C. retained their initial structure and did not degrade (FIG. 3D).

Figure 3F:
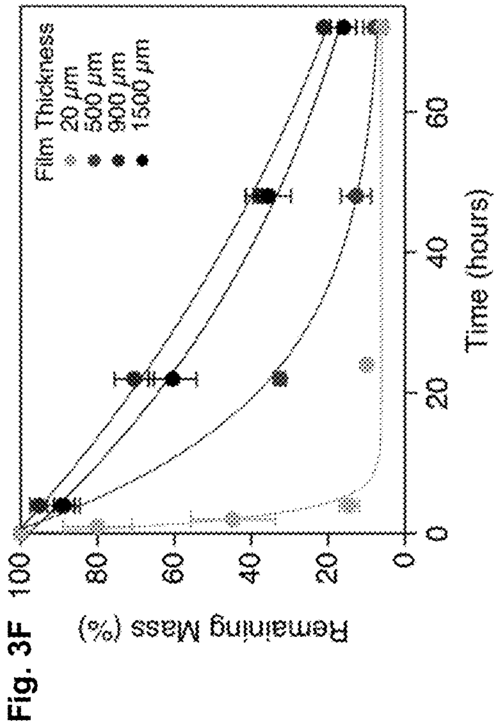
Figure 3E:
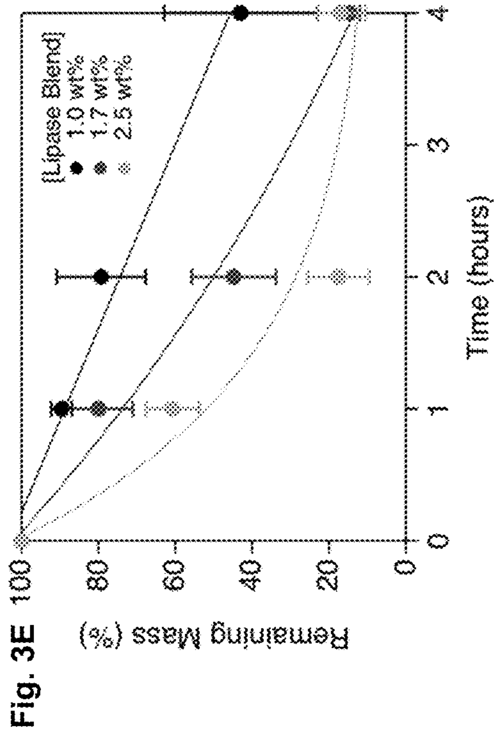

We further demonstrate the scalability of PCL-RHP-lipase degradation using a commercial lipase blend (lipasecb), which can also be embedded nanoscopically in PCL without purifying the enzyme. As shown in fluorescence microscopy (FIG. 14) and TEM (FIG. 15) images and confirmed via dynamic light scattering (DLS) (FIG. 16), RHP-lipasecb forms sub ~300 nm particles in toluene, whereas the blend without RHP is insoluble in toluene. The simplest handle for controlling the degradation rate is lipasecb concentration in as-cast films (FIG. 3E). Film thickness also affects degradation; the degradation rate slows down with increasing film thickness up to ~1 mm, at which point it plateaus (FIG. 3F). The degradation dependence on film thickness is expected, as lipase requires water to carry out successive hydrolysis reactions and thus water diffusion into the hydrophobic PCL matrix is the rate-limiting factor for thicker materials. Given the importance and difficulty of controlling biomedical plastic degradation[20,21] and PCL's FDA approval for use in humans,[22] the ability to tune temporal and spatial degradation of thick (>1 mm) PCL-RHP-lipase materials offers an exciting opportunity to use this system in biomedical applications.

Figure 4A:
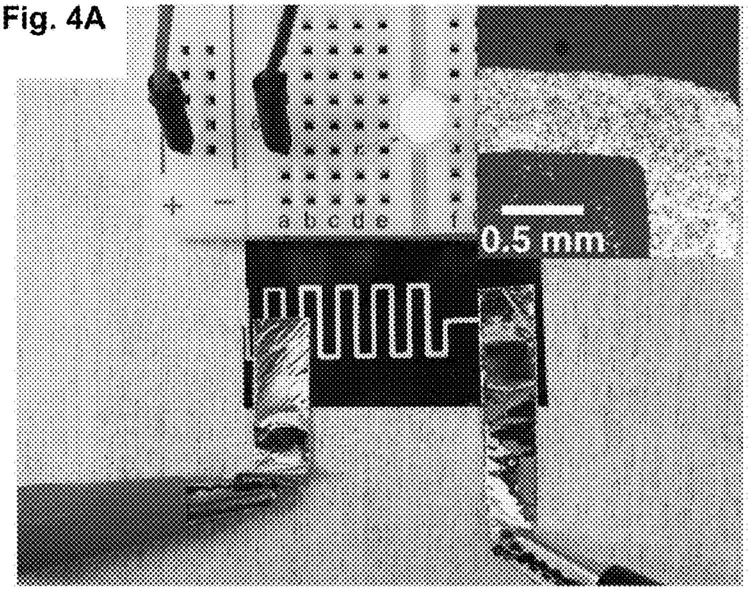
FIGS. 4A-4C. Expansion of RHP-based enzyme embedded plastics for functional applications. A) PCL-RHP-lipase-silver 3-D printed circuit powering a light bulb (inset) SEM image of the 3-D printed circuit; B) recovery of silver flakes after PCL-RHP-lipase degradation via simple filtration; C) conductivity of 3-D printed circuits of PCL with silver, PCL with RHP-lipase-silver, and PCL with the recycled silver.
Figure 4B:
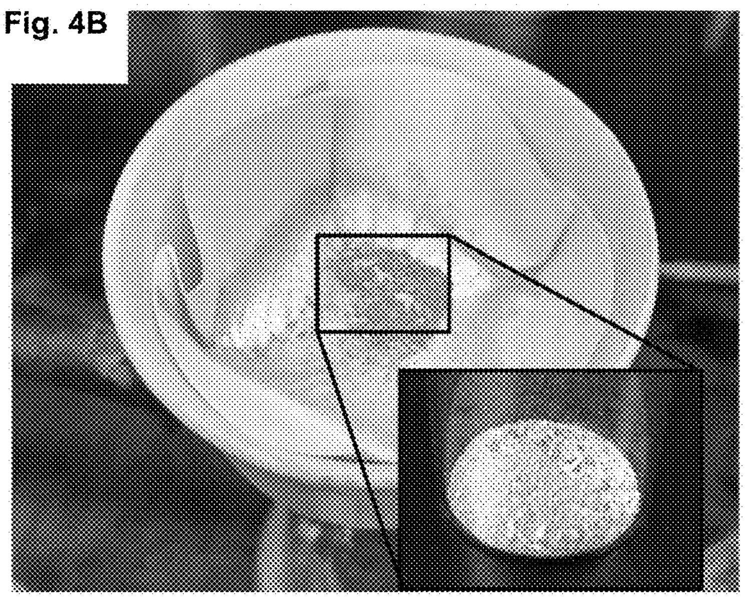
Figure 4C:
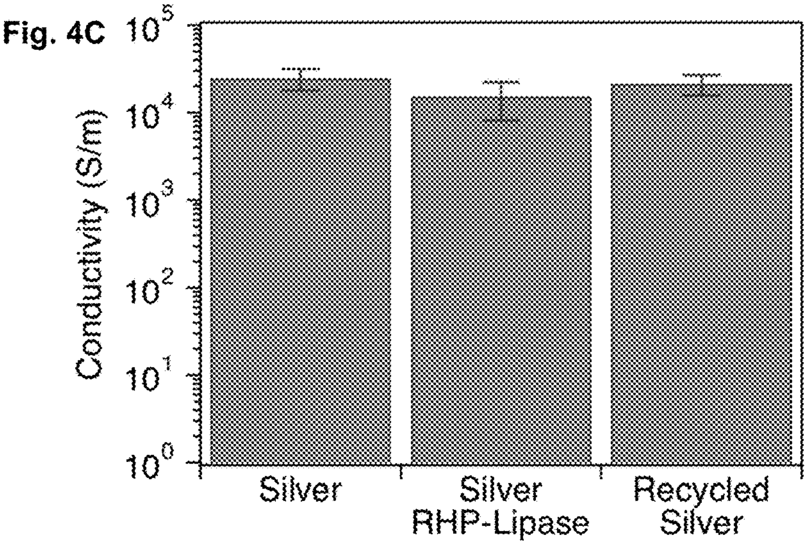

PCL-RHP-lipasecb can be used to formulate conductive ink for 3-D printing of recyclable flexible electronics. Silver flakes and RHP-lipasecb are blended in a concentrated (20 wt %) PCL/toluene solution for printing. With nanoscopic lipase dispersion, the PCL-RHP-lipasecb-silver 3-D printed circuit has high electrical conductivity (FIG. 4A) that expectedly scales with percolation network theory[23,24] (FIG. 17). Incubating the circuit in a 37° C. buffer reduced the current to zero after 4 hours as the enzymatic degradation of PCL matrix disrupting the percolating network of silver flakes (FIG. 18). The material still degrades in a 37° C. buffer even after 7 months of room temperature storage and then 1 month of operation with a 5V potential, confirming the embedded enzymes' long-term stability and resistance to electrical-induced denaturation and deactivation. After degrading PCL-RHP-lipasecb-silver circuits, the silver flakes can be readily collected with high purity (FIG. 4B) and reused without sacrificing electrical conductivity (FIG. 4C). RHP-enzyme inks are attractive for printing high-performance plastics with good recyclability of expensive fillers or for other enzyme-catalyzed applications, especially considering the increasing importance of 3-D printing for functional materials.[25-27]

The concept of nanoscopic enzyme dispersion for plastic degradation is applicable to other plastic-enzyme combinations. Proteinase K degrades poly(lactic acid) (PLA)[28] while lipase does not, likely because proteinase K has a more open, hydrophilic binding pocket that can form a hydrogen bonding network with the repeating PLA ester group (FIG. 19). When RHP-proteinase K is dispersed in PLA, over 50% degradation is observed after 10 days in a 37° C. buffer. PLA-RHP-proteinase K degradation demonstrates the ability to expand the embedded enzyme approach to relevant plastics that are starting to replace nondegradable polyolefins for commodity applications like packaging.[29]

Embedding catalytically-active fillers in plastics offers a viable route toward programmable, on-demand degradation with desirable recycling attributes. Enzyme behavior in a solid matrix may vary significantly once nanoscopically embedded, ranging from substrate binding, by-product, and mechanism of action. The spatial arrangement of catalytically-active particles within plastics and the crystalline properties of the plastic are effective routes to modulate degradation kinetics and pathway. While developing new degradable plastics and green materials has great merit, considering recent developments in synthetic biology and genome information, the rational design of enzyme-embedded plastics provides an immediate, technologically-viable approach to eliminate microplastics and toward control over the complete life cycle of polymers.

Methods

Materials Amano PS Lipase from *Burkholderia cepacia* and Proteinase K from *Tritirachium album* was purchased from Sigma Aldrich. For purified enzyme studies, purification was carried out using a published method.30 For commercial blend studies, the blend was used as-purchased. PCL (80,000 g mole-1, PDI <2) and PLA (85,000-160,000 g/mole) was purchased from Sigma Aldrich, and PS-PCL-PS was purchased from Polymer Source; all were used without further purification. The random heteropolymer (70,000 g mole-1) was synthesized as previously reported.13 3lip and lic6 entries in Protein Data Bank were used for lipase and proteinase k crystal structure representations, respectively. For substrate binding analysis, lys1 and 3prk entries were used for lipase and proteinase K, respectively. PCL-RHP-lipase-silver ink was printed at room temperature from a PCL/toluene (20 wt %) solution containing RHP-lipase and silver flakes. Conductivity was measured using a homemade direct current setup.

Degradation: RHP-lipase complex was mixed in aqueous solution, lyophilized overnight, and resuspended directly in 4 wt % PCL/toluene solution (or proteinase K in 4 wt % PLA/dichloromethane solution). Films were peeled off glass microscope slides when dry and placed in sodium phosphate buffer (25 mM). At given timepoints films were removed, rinsed, and vacuum dried. For PCL-RHP-lipase, up to 5 hours, remaining film mass was measured using a balance.

To estimate remaining microplastic concentration for as-cast films at 24 hours (~95% elimination), gel permeation chromatography (GPC) peaks were manually integrated from 11 to 15 min and the area was divided by that of as-purchased PCL sample because weighing on a balance was not possible due to small particle size and remaining mass. The proof-of-concept repolymerization was carried out using a previously-reported method31 after recovering degraded PCL by-product from enzyme and buffer salts via phase extraction and filtration. For PLA-RHP-proteinase K, degradation was determined by weighing remaining mass at the stated time.

Characterization: Dynamic light scattering was run on a Brookhaven BI-200SM Light Scattering System using a 90° angle. For differential calorimetry (DSC), temperature was ramped from 25° C. to 70° C. at a 2° C. min-1 scan rate. To quantify percent crystallinity, the sample's enthalpy of melting was divided by 151.7 J g-1, enthalpy of melting for 100% crystalline PCL.[32] For uniaxial tensile tests, PCL solutions were cast in custom-designed Teflon molds with standard dog-bone shapes. TEM images were taken on a JEOL 1200 microscope at 120 kV accelerating voltage. 5 wt % ruthenium tetroxide solution was used to stain the RHP-lipase and the amorphous PCL domains.

For small angle x-ray scattering (SAXS) studies, ~300 μm thick films were cast in Teflon beakers. Samples were vacuum dried after degradation for at least 16 hours prior to running SAXS, which was conducted at beamline 7.3.3 at the Advanced Light Source (ALS) at the Lawrence Berkeley National Laboratory. X-rays with 1.24 Å wavelength and 2 s exposure times were used.

For small molecule assays (used to estimate thermostability), films were submerged in 0.5 mM solution of 4-nitrophenyl butyrate in buffer. Activity was monitored using UV-vis spectroscopy to quantify hydrolysis over 20 minutes.

A U-MWBS3 mirror unit with 460-490 nm excitation wavelengths was used for fluorescence microscopy. Commercially-available NHS-Fluorescein (5/6-carboxyfluorescein succinimidyl ester) was used to label lipase by following commercial procedures. The solution was centrifuged in a 10,000 g mole-1 filter to remove excess dye from the labeled lipase.

GPC measurements were obtained using a total concentration of 2 mg/mL of remaining film and by-product in THE 2 uL of solution was injected into an Agilent PolyPore 7.5×300 mm column. Liquid chromatography-mass spectrometry (LCMS) measurements were obtained by resuspending degradation supernatant in acetonitrile/water (67/33 vol %) and running through an Agilent InfinityLab EC-C18, 2.7 μm column. The mass spectrum shown is a combination of the major peaks seen in the chromatogram. Degradation products were dried via lyophilization overnight before resuspending in the proper solvent for GPC or LCMS.

REFERENCES

Law, K. L. & Thompson, R. C. Microplastics in the seas. Science 345, 144-145, doi:10.1126/science.1254065 (2014).

2 Geyer, R., Jambeck, J. R. & Law, K. L. Production, use, and fate of all plastics ever made. Sci Adv 3, e1700782, doi:10.1126/sciadv.1700782 (2017).

3 Jambeck, J. R. et al. Plastic waste inputs from land into the ocean. Science 347, 768-771, doi:10.1126/science.1260352 (2015).

4 Catarino, A. I., Macchia, V., Sanderson, W. G, Thompson, R. C. & Henry, T. B. Low levels of microplastics (MP) in wild mussels indicate that MP ingestion by humans is minimal compared to exposure via household fibres fall-out during a meal. Environ Pollut 237, 675-684, doi:10.1016/j.envpol.2018.02.069 (2018).

5 Setala, O., Fleming-Lehtinen, V. & Lehtiniemi, M. Ingestion and transfer of microplastics in the planktonic food web. Environ Pollut 185, 77-83, doi:10.1016/j.envpol.2013.10.013 (2014).

6 Wei, R. & Zimmermann, W. Microbial enzymes for the recycling of recalcitrant petroleum-based plastics: how far are we? Microb Biotechnol 10, 1308-1322, doi:10.1111/1751-7915.12710 (2017).

7 Wei, R. et al. Turbidimetric analysis of the enzymatic hydrolysis of polyethylene terephthalate nanoparticles. Journal of Molecular Catalysis B: Enzymatic 103, 72-78, doi:10.1016/j.molcatb.2013.08.010 (2014).

8 Mueller, R. J. Biological degradation of synthetic polyesters—Enzymes as potential catalysts for polyester recycling. Process Biochem 41, 2124-2128, doi:10.1016/j.procbio.2006.05.018 (2006).

9 Ganesh, M., Dave, R. N., L'Amoreaux, W. & Gross, R. A. Embedded Enzymatic Biomaterial Degradation. Macromolecules 42, 6836-6839, doi:10.1021/ma901481h (2009).

10 Zan, L. et al. Solid-phase photocatalytic degradation of polystyrene with modified nano-TiO2 catalyst. Polymer 47, 8155-8162, doi:10.1016/j.polymer.2006.09.023 (2006).

11 Klibanov, A. M. Why are enzymes less active in organic solvents than in water? Trends Biotechnol 15, 97-101, doi:10.1016/50167-7799(97)01013-5 (1997).

12 Klibanov, A. M. Improving enzymes by using them in organic solvents. Nature 409, 241-246, doi:10.1038/35051719 (2001).

13 Panganiban, B. et al. Random heteropolymers preserve protein function in foreign environments. Science 359, 1239-1243, doi:10.1126/science.aao0335 (2018).

14 DelRe, C. et al. Reusable Enzymatic Fiber Mats for Neurotoxin Remediation in Water. Acs Appl Mater Inter 10, 44216-44220, doi:10.1021/acsami.8b18484 (2018).

15 Khan, I., Nagarjuna, R., Dutta, J. R. & Ganesan, R. Enzyme-Embedded Degradation of Poly(epsilon-caprolactone) using Lipase-Derived from Probiotic *Lactobacillus plantarum*. Acs Omega 4, 2844-2852, doi:10.1021/acsomega.8b02642 (2019).

16 Kobayashi, S., Uyama, H. & Takamoto, T. Lipase-catalyzed degradation of polyesters in organic solvents, a new methodology of polymer recycling using enzyme as catalyst. Biomacromolecules 1, 3-5, doi:10.1021/bm990007c (2000).

17 Pleiss, J., Fischer, M. & Schmid, R. D. Anatomy of lipase binding sites: the scissile fatty acid binding site. Chem Phys Lipids 93, 67-80, doi:10.1016/S0009-3084(98)00030-9 (1998).

18 Horn, S. J. et al. Costs and benefits of processivity in enzymatic degradation of recalcitrant polysaccharides. P Natl Acad Sci USA 103, 18089-18094, doi:10.1073/pnas.0608909103 (2006).

19 Beckham, G T. et al. Molecular-Level Origins of Biomass Recalcitrance: Decrystallization Free Energies for Four Common Cellulose Polymorphs. J Phys Chem B 115, 4118-4127, doi:10.1021/jp1106394 (2011).

20 Washington, M. A. et al. The impact of monomer sequence and stereochemistry on the swelling and erosion of biodegradable poly(lactic-co-glycolic acid) matrices. Biomaterials 117, 66-76, doi:10.1016/j.biomaterials.2016.11.037 (2017).

21 Li, J., Stayshich, R. M. & Meyer, T. Y. Exploiting Sequence To Control the Hydrolysis Behavior of Biodegradable PLGA Copolymers. Journal of the American Chemical Society 133, 6910-6913, doi:10.1021/ja2008955 (2011).
22 Woodruff, M. A. & Hutmacher, D. W. The return of a forgotten polymer-Polycaprolactone in the 21st century. Frog Polym Sci 35, 1217-1256, doi:10.1016/j.progpolymsci.2010.04.002 (2010).
23 Valentine, A. D. et al. Hybrid 3D Printing of Soft Electronics. Adv Mater 29, doi:10.1002/adma.201703817 (2017).
24 Stauffer, D. & Aharony, A. Introduction to Percolation Theory: Second Edition. (CRC Press, 1994).
25 Muth, J. T. et al. Embedded 3D Printing of Strain Sensors within Highly Stretchable Elastomers. Adv Mater 26, 6307-6312, doi:10.1002/adma.201400334 (2014).
26 Zarek, M. et al. 3D Printing of Shape Memory Polymers for Flexible Electronic Devices. Adv Mater 28, 4449-4454, doi:10.1002/adma.201503132 (2016).
27 Lind, J. U. et al. Instrumented cardiac microphysiological devices via multimaterial three-dimensional printing. Nat Mater 16, 303-308, doi:10.1038/Nmat4782 (2017).
28 Li, S. M. & McCarthy, S. Influence of crystallinity and stereochemistry on the enzymatic degradation of poly (lactide)s. Macromolecules 32, 4454-4456, doi:10.1021/ma990117b (1999).
29 Farah, S., Anderson, D. G & Langer, R. Physical and mechanical properties of PLA, and their functions in widespread applications—A comprehensive review. Adv Drug Deliver Rev 107, 367-392, doi:10.1016/j.addr.2016.06.012 (2016).
30 Bornscheuer, U. et al. Lipase of *Pseudomonas-Cepacia* for Biotechnological Purposes—Purification, Crystallization and Characterization. Bba-Gen Subjects 1201, 55-60, doi:10.1016/0304-4165(94)90151-1 (1994).
31 Schindler, A., Hibionada, Y. M. & Pitt, C. G Aliphatic Polyesters 0.3. Molecular-Weight and Molecular-Weight Distribution in Alcohol-Initiated Polymerizations of Epsilon-Caprolactone. J Polym Sci Pol Chem 20, 319-326, doi:10.1002/pol.1982.170200206 (1982).
32 Wurm, A. et al. Crystallization and Homogeneous Nucleation Kinetics of Poly(epsilon-caprolactone) (PCL) with Different Molar Masses. Macromolecules 45, 3816-3828, doi:10.1021/ma300363b (2012).

The invention claimed is:

1. A bioactive plastic composition comprising an organic polymer and a nanoscopic dispersion of complexes of random heteropolymers and an enzyme that hydrolyzes the polymer, such that hydrolysis of the polymer by the enzyme imparts depolymerization and microplastic elimination, wherein the complexes are uniformly distributed within the composition, the complexes range in size from 10 nm to 500 nm, wherein the size of the complexes is the hydrodynamic diameter of the complexes, the composition comprises 0.001 to 5 wt % enzyme content, and wherein the random heteropolymers comprise varying ratios of a plurality of monomers selected from methyl methacrylate (MMA), oligo (ethylene glycol) methacrylate (OEGMA), 3-sulfopropyl methacrylate potassium salt (3-SPMA) and 2-ethylhexyl methacrylate (2-EHMA) wherein polymer/enzyme combinations are selected from selected from polycaprolactone/lipase, polylactic acid/proteinase K, and polyethylene terephthalate/PETase.

2. The composition of claim 1, wherein the complexes range in size from 10 nm to 200 nm.

3. The composition of claim 1, wherein the complexes range in size from 20 nm to 200 nm.

4. The composition of claim 1, wherein the complexes range in size from 10 nm to 100 nm.

5. The composition of claim 1, wherein the complexes range in size from 20 nm to 100 nm.

6. The composition of claim 1, wherein the enzyme content is 0.001 to 1 wt %.

7. The composition of claim 1, wherein the enzyme content is 0.01 to 1 wt %.

8. The composition of claim 1, wherein the enzyme content is 0.001 to 0.1 wt %.

9. The composition of claim 1, wherein the enzyme content is 0.01 to 0.1 wt %.

10. The composition of claim 1, wherein the complexes range from 10 nm to 500 nm between crystalline polymer lamellae of the composition.

11. The composition of claim 1, wherein the complexes range from 10 nm to 200 nm between crystalline polymer lamellae of the composition.

12. The composition of claim 1, wherein the complexes range from 10 nm to 100 nm between crystalline polymer lamellae of the composition.

13. The composition of claim 1, wherein the complexes range from 40 nm to 100 nm between crystalline polymer lamellae of the composition.

14. The composition of claim 1, formulated in a conductive ink for 3-D printing.

15. The composition of claim 1, formulated in a conductive ink for 3-D printing and comprising a precious metal filler, wherein the method provides 50 to 99% recovery of the precious metal filler.

16. The composition of claim 1, configured to provide continuous degradation of the organic polymer and achieve 95% microplastic elimination.

17. The composition of claim 1, configured to provide a polymer-based degradation mechanism with repolymerizable small molecule by-products via selective chain end scission rather than random chain scission.

18. The composition of claim 1, configured to provide spatially- and temporally-programmable degradation of melt- or solution-processed host matrix due to the dependence of polymer degradation on local lamellae thickness regardless of bulk percent crystallinity.

19. A method of programmable degradation and microplastic elimination, the method comprising:

providing a bioactive plastic composition of claim 1; and maintaining the composition under conditions wherein the enzyme cleaves the polymer backbone to achieve programmable degradation and microplastic elimination.

* * * * *